(12) United States Patent
Brookoff

(10) Patent No.: US 8,946,209 B2
(45) Date of Patent: Feb. 3, 2015

(54) COMPOSITIONS AND METHODS FOR TREATING AND PREVENTING UROLITHIASIS AND CONDITIONS ASSOCIATED THEREWITH

(75) Inventor: Daniel Brookoff, Memphis, TN (US)

(73) Assignee: OptMed, Inc., New York, NY (US)

( * ) Notice: Subject to any disclaimer, the term of this patent is extended or adjusted under 35 U.S.C. 154(b) by 297 days.

(21) Appl. No.: 12/768,994

(22) Filed: Apr. 28, 2010

(65) Prior Publication Data

US 2010/0272806 A1 Oct. 28, 2010

Related U.S. Application Data

(60) Provisional application No. 61/260,575, filed on Nov. 12, 2009, provisional application No. 61/173,403, filed on Apr. 28, 2009.

(51) Int. Cl.

| | | |
|---|---|---|
| *A61K 31/55* | (2006.01) | |
| *A61K 31/5513* | (2006.01) | |
| *A61K 9/00* | (2006.01) | |
| *A61K 9/06* | (2006.01) | |
| *A61K 47/10* | (2006.01) | |
| *A61K 47/24* | (2006.01) | |
| *A61K 47/38* | (2006.01) | |

(52) U.S. Cl.
CPC .......... *A61K 31/5513* (2013.01); *A61K 9/0034* (2013.01); *A61K 9/06* (2013.01); *A61K 47/10* (2013.01); *A61K 47/24* (2013.01); *A61K 47/38* (2013.01)
USPC ........................................................ 514/221

(58) Field of Classification Search
USPC ........................................................ 514/221
See application file for complete search history.

(56) References Cited

U.S. PATENT DOCUMENTS

| | | | |
|---|---|---|---|
| 6,193,985 | B1 | 2/2001 | Sonne |
| 7,419,976 | B2 | 9/2008 | Oberhauser et al. |
| 7,521,424 | B2 | 4/2009 | Rosen et al. |
| 2006/0030622 | A1 * | 2/2006 | Mak et al. ............ 514/509 |

FOREIGN PATENT DOCUMENTS

WO 2007/147505 12/2007

OTHER PUBLICATIONS www.jointandbackpain.com/Kidney_Stones.html.*
www.angelfire.com/planet/k3h3y/diazepam-suppositories.html.*
Rutherford et al Br. J. Clin Pharmac (1978), 6, 69-73.*
Ferdinando et al (Journal of Endourology. 2002, 16(supplement 1): 33-187; Poster session).*
Ratnar Pain, 8(5); 2000.*
GW Medical Faculty Associates Heart and Vascular 2008, Apr. 7.*
www.angelfire.com/planet/k3h3y/diazepam-suppositories, htm (2008) corrected for May 8, 2012.*
www.jointandbackpain.com/Kidney_Stones.html Mar. 25, 2009 (corrected for May 8, 2012.*
International Search Report for International Application No. PCT/US2010/032708, dated Jul. 2, 2010.
Chan, P. S. F., et al., "Transurethral Ureterorenoscopic Lithotripsy and Retrieval of Ureteric Calculi Under Local Anaesthesia and Sedation," British Journal of Urology, vol. 65, pp. 141-143 (Feb. 1990).
Bauer, E., et al., "ESWL Management of Ureteral Calculi Without Anesthesia: An Alternative to Invasive Procedures," European Urology, vol. 16, pp. 405-409 (1989).
Tiselius, Hans-Goran, "Anesthesia-Free in Situ Extracorporeal Shock Wave Lithotripsy of Ureteral Stones," The Journal of Urology, vol. 146, pp. 8-12 (Jul. 1991).
Supplementary European Search Report issued for European Patent Application No. EP 10 77 0241, dated Oct. 10, 2012.

* cited by examiner

*Primary Examiner* — Shirley V Gembeh
(74) *Attorney, Agent, or Firm* — Pearl Cohen Zedek Latzer Batartz LLP

(57) ABSTRACT

Compositions and methods for the treatment of urinary calculi and fragments thereof are provided. Compositions and methods for the prevention and/or treatment of renal and urinary colic caused by urinary calculi or fragments are also provided. Such compositions and methods provide locally effective amounts of diazepam sufficient to prevent formation of and/or expel ureteral calculi and fragments thereof and thus prevent and/or treat pain associated with calculi and fragments thereof.

17 Claims, 3 Drawing Sheets

COMPOSITIONS AND METHODS FOR TREATING AND PREVENTING UROLITHIASIS AND CONDITIONS ASSOCIATED THEREWITH

CROSS-REFERENCE TO RELATED APPLICATIONS

This application claims priority to and benefit from U.S. Provisional Application No. 61/173,403 filed on Apr. 28, 2009 and U.S. Provisional Application No. 61/260,575 filed on Nov. 12, 2009, the contents of which are incorporated herein by reference in their entirety.

FIELD OF THE INVENTION

This invention relates to the field of urology. In particular, the invention provides compositions and methods for treating or preventing urolithiasis and conditions associated therewith.

BACKGROUND OF THE INVENTION

In America and Western Europe, renal/ureteral calculi (stones) occur at least once in the lifetimes of 12-15% of men and 4-6% of women. The annual incidence of renal/ureteral stones has been reported to be around 2-3% of this population. The most common presenting symptom is severe flank pain which is often referred to as "acute ureteral colic" or "renal colic." The stones need to be removed via urologic procedures in a third of patients with renal colic, amounting to approximately 500-750 stone-removal procedures per million people annually. Approximately half of the patients with previous urinary calculi have a recurrence within 10 years. Medical emergencies related to stones include unrelieved pain, ureteral obstruction, anuria, infection and acute renal failure, all of which are common reasons for acute hospitalization.

Initial management of kidney and ureteral stones is based on three key concepts: (1) fast and rational diagnostic process; (2) effective pain control; and (3) understanding of the impact of stone location and size on the natural course of the disease. Size of the stone is usually the primary determinant of initial treatment. Stones <5 mm usually pass spontaneously while stones greater than 5 mm are best treated with lithotripsy. More complex stones may require ureteroscopy.

Until little more than 25 years ago, having a ureteral stone >5 mm meant undergoing open surgery. The widespread introduction of devices for extracorporeal shock wave lithotripsy ("ESWL") greatly reduced the need for such invasive procedures. Studies over the past 25 years have shown that on discharge from ESWL, a third of the patients were stone free, while the remainder had stone dust or passable fragments. At 3-month follow-up the stone-free rate was 65%, and at two years 55% were stone free. Overall, recurrence was observed in 14% and regrowth of fragments was seen in 22% of patients. Residual fragments considered by some to be "clinically insignificant" actually may present an important risk factor for recurrence of stones. These patients certainly need to be monitored and ultimately may need to be pre-emptively treated. Over 20% of patients with persistent residual fragments develop new stones at the site of the fragments.

ESWL has become the standard of treatment for large ureteral calculi and provides an overall stone-free rate of 86-90% for stones <10 mm. One drawback of ESWL, however, is that it often requires repeated treatments. Ultimately, up to 98% of stones can be successfully fragmented by ESWL, but the ability of the kidneys and urethers to clear the resulting fragments is critically important in terms of successful treatment outcomes in that residual lithiases tend to result in re-growth and further progression of stone disease.

Limitations of ESWL include unknown ovarian effects in women of child-bearing age who have middle or distal ureter stones and bleeding disorders. Recent use of NSAIDs is another contraindication to ESWL because of increased risk of perinephric bleeding. Patients should discontinue use of NSAIDS at least 3 days prior to ESWL. ESWL also has been reported to cause renal (subcapsular and perirenal) hematomas which can be responsible for persistent lumbar pain.

Another approach to stones that are not expected to pass spontaneously is ureteroscopy ("URS"). Stones larger than 10 mm are generally better treated with ureteroscopy. However, most urologists prefer ESWL to URS as a first-line treatment because it is less invasive and, unlike URS, it does not require general anesthesia.

A comparison of URS to ESWL indicates shorter hospital stays for the ESWL group. Retreatment rates were lower (but did not reach significance) in the URS group. On the other hand, URS achieves a higher stone-free rate but at the cost of higher complication rates and longer hospital stays. URS is preferred in females of child-bearing age (due to concern about ovarian damage due to ESWL), patients with impacted stones, obstructive uropathy, stones >2 cm and radiotransparent stones. A major disadvantage of ESWL lies in the number of repetitions required and the long wait—often months—until the last fragments pass. However, the need for anesthesia in URS has to be factored in when comparing the two procedures.

Up to 75% of kidney stones will spontaneously pass without the need of ESWL or URS. Two thirds of ureteral stones that pass spontaneously will pass within four weeks after the onset of the symptoms; however, a ureteral stone that has not passed in 4-8 weeks is unlikely to pass spontaneously, and stones that have not passed within 4 weeks have a major complication rate of about 20%. Repeated imaging is warranted to confirm passage of the stone because inappropriate (or unsuccessful) watchful waiting can result in severe and even life-threatening complications such as intractable ureteral strictures (causing chronic pain), anuria, renal failure and sepsis. Even when successful, spontaneous passage of a stone can be painful and temporarily debilitating. Medical treatment and watchful waiting are associated with pain and significant loss of work days.

ESWL and URS are not free of risks and are relatively expensive. An appropriate conservative approach to stone expulsion is generally more cost-effective than any invasive procedure, but only if it results in timely expulsion of the stone. Failure of conservative treatment is far more costly than immediate URS or ESWL because of missed worked days and the need for complex urological care. Overall, watchful waiting without any additional medical treatment results in 25-54% expulsion rates with a mean expulsion time of >10 days and considerable analgesic use even when the stones are <4 mm.

The high incidence of complications of kidney stones has prompted a search for a useful medical (pharmacologic) therapy. As discussed in more detail below, these therapies have included a myriad of intravenous hydration and diuretics, steroids, opioids, progesterone, calcium channel blockers, and alpha-1 blockers, along with the use of various combinations of the foregoing.

The longest-used approach to promote the passage of ureteral stones was vigorous intravenous hydration with the use of diuretics aimed at increasing the pressure in the proximal ureter in order to "push" the stone out. However, a recent review found no credible evidence supporting the use of high volume intravenous fluids or diuretics for the treatment of acute ureteral colic, and such treatment does not address the pain associated with colic.

Methylprednisolone has shown some marginal benefit in facilitating passage of ureteral stones (usually in conjunction with other medications), but has to be used with caution in patients with cardiac disease, hypertension or renal insufficiency. The combination of steroids and nifedipine seems to help in the expulsion of small distal ureteral stones of <1.5 mm.

While opioids are supposed to be the "gold standard" for the treatment of severe pain, it has been found that they are not very effective for ureteral colic and may even hinder the passage of stones.

Hydroxyprogesterone may hasten stone passage and may account for the reduced incidence of symptomatic stones in women.

While some investigators feel that calcium channel blockers increase the rate of spontaneous stone passage in patients who are good candidates for conservative management, others feel that calcium channel blockers have no value in the management of acute ureteral colic.

Many potentially expulsive drugs that have been shown to be effective in animal studies have found limited use in humans due to side effects and toxicities. These include certain antihistamines, parasympatholytic agents and prostaglandins E1 and E2 analogues. Ureteral antispasmodics such as phentolamine and theophylline have shown some effect but their use has been limited by toxicity. The action of nitric oxide (after administration of nitroprusside or glycerol trinitrate ["GTN"]) is to inhibit smooth muscle in the upper urinary tract suggesting potential use of nitric oxide promoters for stone expulsion. In human studies, GTN was mildly effective compared to scopolamine with increased side effects in the GTN group. A trial of GTN patches, however, showed no advantages over placebo for stone passage or for relief of ureteral colic.

Alpha-1 receptor antagonists inhibit basal ureteral tone and decrease peristaltic frequency and amplitude. Muscle cells of the lower urinary tract express two types of alpha-1 receptors (alpha and delta). An inhibitor of these receptors, tamsulosin (Flomax) has been used for years for the treatment of lower urinary tract symptoms in men with prostatism. Tamsulosin significantly reduces ureteral pressure but has no effect on contraction frequency. Tamsulosin has found increasing use as a promoter of stone expulsion in similar doses to those used for lower urinary tract symptoms. At the doses used, the most common reported side effects of tamsulosin are abnormal ejaculation, dizziness and rhinitis.

All of the foregoing treatments are of limited effectiveness, especially with larger calculi. Many of these treatments are associated with significant side effects limiting their usefulness. Accordingly, there remains a great need for improved compositions and methods for treating and preventing urolithiasis and conditions associated therewith.

SUMMARY OF THE INVENTION

This invention relates to the surprising discovery that local delivery of an effective amount of a pharmaceutical composition comprising diazepam is capable of treating and preventing urolithiasis and conditions associated therewith, without the side effects often associated with previous treatments.

In one embodiment the present invention provides compositions and methods for treating a mammal having kidney and/or urinary stones.

In another embodiment the present invention provides compositions and methods for preventing renal or ureteral colic caused by kidney or ureteral stones or fragments, or re-formation of kidney or ureteral stones.

DETAILED DESCRIPTION OF THE INVENTION

Figure 1:
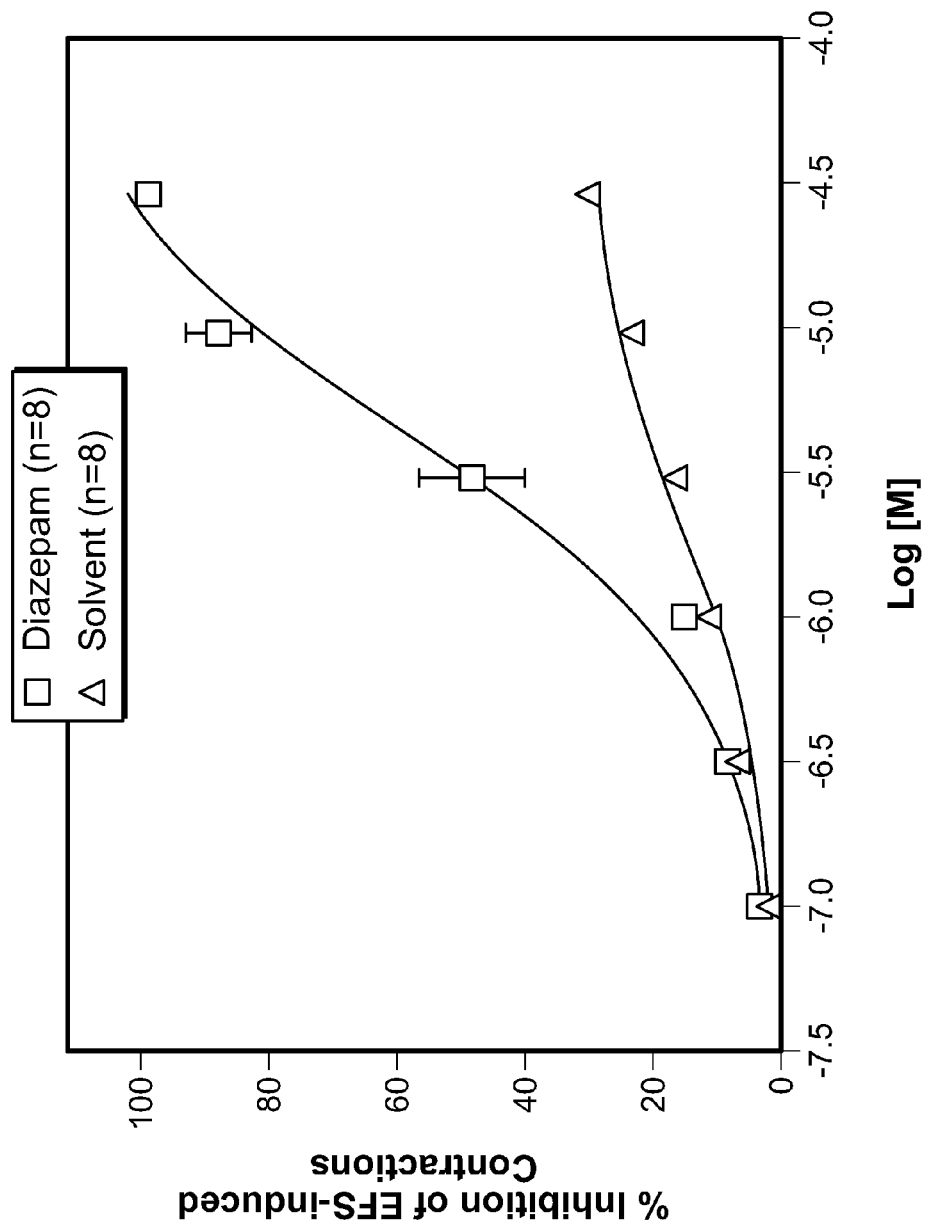
FIG. 1 provides results of Electric Field Stimulation ("EFS")-induced contractions in isolated human ureteral tissue.

As used herein, a "pharmaceutical composition" refers to any combination of two or more components. It may be in the form of, for example, a solution, a suspension, liquid, powder, a paste, aqueous, non-aqueous or any combination thereof.

The term "diazepam" is used herein to refer to 7-chloro-1, 3-dihydro-1-methyl-5-phenyl-2H-1,4-benzodiazepin-2-one and all pharmaceutically-acceptable forms and its derivatives.

By an "effective amount" is meant a nontoxic, but sufficient, amount of diazepam needed to promote the expulsion of ureteral stones or fragments. An effective amount of diazepam is preferably less than about 50 mg. In certain embodiments an effective amount is from about 1 mg to about 30 mg. In other embodiments an effective amount is from about 5 mg to about 20 mg. In certain embodiments, an effective amount is less than about 5 mg.

The present invention relates to the surprising discovery that the delivery of locally effective amounts of diazepam is surprisingly effective in promoting the expulsion of ureteral stones and stone fragments in mammals, especially in humans and canine and feline species.

Dosage Forms

Dosage forms for local administration of diazepam may include for example ointments, pastes, creams, lotions, gels and solutions. The active ingredient may be mixed under sterile conditions with a pharmaceutically-acceptable carrier.

Dosage forms may contain, in addition to diazepam, carriers or excipients, such as animal and vegetable fats, oils, waxes, paraffins, starch, tragacanth, cellulose derivatives, polyethylene glycols, propylene glycols, glycerine, silicones, bentonites, silicic acid, talc and zinc oxide, other synthetic solvents, or mixtures thereof.

Solutions generally consist of homogeneous mixtures of a pharmacologically active substance in a solvent. Gels generally comprise a liquid organic phase entrapped in a three-dimensionally cross-linked network. The liquid may be an organic solvent, a mineral oil or a vegetable oil. Sprays generally include a dynamic collection of liquid drops and entrained surrounding gas. Suspensions generally include dispersions of solid particles in fluids. Pastes generally include suspensions of small particles dispersed in a background fluid comprising a fatty base (e.g., petroleum jelly) and generally 25% or more of a solid substance (e.g., zinc oxide).

Ointments are semisolid preparations which are typically based on petrolatum or other petroleum derivatives. As with other carriers or vehicles, an ointment base should be inert, stable, nonirritating and nonsensitizing. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

Specific example of emulsifiers and surfactants include: nonionic ethoxylated and nonethoxylated surfactants, abietic acid, almond oil polyethylene glycol, beeswax, butylglucoside caprate, $C_{18}$-$C_{36}$ acid glycol ester, $C_9$-$C_{15}$ alkyl phosphate, caprylic/capric triglyceride polyethylene glycol-4 esters, ceteareth-7, cetyl alcohol, cetyl phosphate, corn oil polyethylene glycol esters, dextrin laurate, dilaureth-7 citrate, dimyristyl phosphate, glycereth-17 cocoate, glyceryl erucate, glyceryl laurate, hydrogenated castor oil polyethylene glycol esters, isosteareth-11 carboxylic acid, lecithin, lysolecithin, nonoxynol-9, octyldodeceth-20, palm glyceride, polyethylene glycol diisostearate, polyethylene glycol stearamine, poloxamines, potassium linoleate, raffinose myristate, sodium caproyl lactylate, sodium caprylate, sodium cocoate, sodium isostearate, sodium tocopheryl phosphate, steareths, and trideceths, aluminum starch octenylsuccinate, ammonium hydroxide, amphoteric-9, beeswax, synthetic beeswax, carbomer 934, carbomer 934P, carbomer 940, ceteareth-20, ceteareth-30, cetearyl alcohol, ceteth 20, cetyl alcohol, cholesterol, cyclomethicone, diglycerides, dimethicone (e.g., dimethicone 350), disodium monooleamidosulfosuccinate, NF emulsifying wax, fatty acid pentaerythritol ester, glycerides, glyceryl monooleate, glyceryl monostearate, lanolin, lanolin alcohol, hydrogenated lanolin, magnesium stearate, mineral oil, monoglycerides, polyethylene glycol, PEG 100 stearate, polyethylene glycol 6000 distearate, polyethylene glycol 1000 monocetyl ether, polyethylene glycol monostearate, polyethylene glycol 400 monostearate, polyoxyethylene glycol fatty alcohol ethers, polyoxyl 20 cetostearyl ether, polyoxyl 40 stearate, polysorbate 20, polysorbate 40, polysorbate 60, polysorbate 80, polysorbates, PPG-26 oleate, propylene glycol stearate, quaternium-15, simethicone, sodium laureth sulfate, sodium lauryl sulfate, sorbitan esters, sorbitan monolaurate, sorbitan monooleate, sorbitan monopalmitate, sorbitan monostearate, sorbitan palmitate, sorbitan sesquioleate, steareth-2, steareth-100, stearic acid, stearyl alcohol, triethanolamine and trolamine. Other surfactants and emulsifiers may be used, as will be appreciated by one of ordinary skill in the art.

Compositions according to the present invention also may include a wide range of other optional ingredients including, antifoaming agents; buffers, neutralizing agents and agents to adjust pH; coloring agents and decoloring agents; emollients and emulsion stabilizers; humectants; odorants; preservatives, antioxidants, and chemical stabilizers; solvents; and stiffening and suspending agents. Exemplary antifoaming agents include cyclomethicone, dimethicone (e.g., dimethicone 350) and simethicone. Exemplary buffers, neutralizing agents and agents to adjust pH include ammonium hydroxide, citric acid, diisopropanolamine, hydrochloric acid, lactic acid, monobasic sodium phosphate, sodium citrate, sodium hydroxide, sodium phosphate, triethanolamine, and trolamine. Exemplary emollients include caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol and urea.

Exemplary emulsion stabilizers and viscosity builders include carbomer 934, carbomer 934P, carbomer 940, cetearyl alcohol, cetostearyl alcohol, cetyl alcohol, cetyl stearyl alcohol, dextrin, diglycerides, disodium edetate, edetate disodium, glycerides, glyceryl monostearate, glyceryl stearate, hydroxypropyl cellulose, monoglycerides, plasticized hydrocarbon gel, polyethylene glycol 300, polyethylene glycol 400, polyethylene glycol 1450, polyethylene glycol 8000, polyethylene glycols, propylene glycol stearate and stearyl alcohol. Exemplary humectants include glycerine, propylene glycol, sorbitol and urea. Exemplary odorants include hypoallergenic perfume, menthol. Exemplary preservatives, antioxidants, and chemical stabilizers include alcohol, benzyl alcohol, butylated hydroxyanisole, butylated hydroxytoluene, butylparaben, calcium acetate, caster oil, chlorocresol, 4-chloro-m-cresol, citric acid, disodium edetate, Dowicil 200 (Dow), edetate disodium, ethoxylated alcohol, ethyl alcohol, glycerin, Glydant Plus (Lonza), 1,2,6-hexanetriol, Kathon CG (Rohm & Haas), Liquid Germall Plus (ISP Sutton Labs), Liquipar (ISP Sutton Labs), methylparaben, parabens, potassium sorbate, propyl gallate, propylene glycol, propylparaben, sodium bisulfite, sodium citrate, sodium metabisulfite, sorbic acid, tannic acid, triglycerides of saturated fatty acids, Ucarcide (Union Carbide), and zinc stearate. Exemplary solvents include alcohol, castor oil, diisopropyl adipate, ethoxylated alcohol, ethyl alcohol, fatty alcohol citrate, glycerin, 1,2,6-hexanetriol, hexylene glycol, isopropyl alcohol, isopropyl myristate, isopropyl palmitate, mineral oil, phosphoric acid, polyethylene glycol 300, polyethylene glycol 400, polyethylene glycol 1450, polyethylene glycol 8000, polyethylene glycol 1000 monocetyl ether, polyethylene glycol monostearate, polyethylene glycol 400 monostearate, polyethylene glycols, polyoxyl 20 cetostearyl ether, polyoxypropylene 15-stearyl ether, polysorbate 20, polysorbate 40, polysorbate 60, polysorbate 80, polysorbates, propylene carbonate, propylene glycol, purified water, and SD alcohol 40, triglycerides of saturated fatty acids.

Examples of thickening, stiffening and suspending agents that are suitable for inclusion in compositions according to the present invention may include agents commonly used in skin care preparations. More specifically, such excipients include acrylamides copolymer, agarose, amylopectin, calcium alginate, calcium carboxymethyl cellulose, carbomer, carboxymethyl chitin, cellulose gum, dextrin, gelatin, hydrogenated tallow, hydroxyethylcellulose, hydroxypropylcellulose, hydroxypropyl starch, magnesium alginate, methylcellulose, microcrystalline cellulose, pectin, various polyethylene glycol's, polyacrylic acid, polymethacrylic acid, polyvinyl alcohol, various polypropylene glycols, sodium acrylates copolymer, sodium carrageenan, xanthan gum, yeast beta-glucan, aluminum stearate, beeswax, synthetic beeswax, carbomer 934, carbomer 934P, carbomer 940, cetostearyl alcohol, cetyl alcohol, cetyl esters wax, dextrin, glyceryl monostearate, hydroxypropyl cellulose, kaolin, paraffin, petrolatum, polyethylene, propylene glycol stearate, starch, stearyl alcohol, wax, white wax, xanthan gum, and bentonite. Thickening agents other than those listed above may also be used in related embodiments of the present invention.

In one embodiment of the present invention pharmaceutical formulations include diazepam in a matrix-based gel. Such matrix-based gels may include carbomer and/or hydroxycellulose, polycarbophils, propylene glycol, glycerin and water. In another embodiment suitable formulations may be in the form of vesicle/inclusion-based creams which may include lipids and/or beta cyclodextrin in a hydrophilic cream base.

Such formulations optionally may include preservatives such as sorbic acid and/or benzyl alcohol. In one embodiment sorbic acid may be used as a preservative in matrix-based gels. In other embodiment benzyl alcohol may be used as a preservative in a vesicle/inclusion-based cream. In certain embodiments other preservatives may be used in addition to or instead of sorbic acid and/or benzyl alcohol.

In certain embodiments pharmaceutical formulations also may include various organic solvents to increase the solubility of diazepam. Other FDA-approved excipients may be included as well.

In certain embodiments the formulations are adjusted to a pH level between about 3 and 6, more preferably between about 4 and 5.

Representative formulations may include diazepam at concentrations from about 1 to about 20 mg/ml. Specific concentrations within this range may be prepared. For example, in certain embodiments diazepam concentrations may be formulated to include 2, 5 or 10 mg/ml.

Each composition disclosed herein may be packaged in a container appropriate for its viscosity and intended use by the patient. For example, a cream may simply be stored in a non-deformable bottle, or in a squeeze container (such as a tube), or a lidded jar. Such formulations may be stored at room temperature and are preferably protected from light. Care should be taken for storing such formulations since diazepam is incompatible with certain types of plastics.

Local Delivery

Formulations according to the present invention can be delivered into the bladder either by intraurethral injection or by instillation through a bladder catheter allowing diazepam to reach a concentration sufficient to promote the quick expulsion of ureteral stones or fragments without the need for invasive procedures such as cystoscopy. Accordingly, this method can find applications in the emergency department of a hospital, in the doctor's office or even at home.

Additionally, the diazepam formulation could be injected directly into the ureter via a cystoscope which could be performed in an emergency department, a urologist's office or in a surgery center. This would allow for the delivery of the maximal dose to the affected area of obstructed ureter. This could result in the expulsion of a stone or a fragment without risks associated with ESWL, such as hemorrhage, or ureteroscopy, which requires general anesthesia.

Compositions according to the present invention may be administered as an adjuvant to ESWL, increasing its effectiveness in clearing ureters of calculi and fragments thereby reducing the need for repeated procedures.

Diazepam also may be instilled locally as "maintenance therapy" in patients with retained fragments or for patients who tend to re-form ureteral stones. Efforts to stop formation of recurrent stones have so far been insufficient and people with histories of stones usually fail to undertake preventive measures because generally there are no symptoms between episodes of renal colic. Preventive treatments currently include lifelong modifications in diet, drinking habits and other lifestyle factors or lifetime adherence to a pharmacological treatment. Such subjects can be periodically monitored using inexpensive imaging techniques (e.g., plain radiography or ultrasound) and treated with intravesicular or intraureteral diazepam formulations before they become symptomatic.

Cognitive impairment is usually not associated with plasma levels below 100 ng/ml of plasma. Following the administration of an effective amount of diazepam-containing compositions, the maximum plasma level of diazepam and of its primary active metabolite, desmethyldiazepam, preferably will not exceed 100 ng/ml of plasma, preferably will not exceed 50 ng/ml of plasma and even more preferably will not exceed 25 ng/ml of plasma. Local delivery of diazepam thus eliminates, or greatly reduces, cognitive impairment associated with traditional oral or parenteral use.

It is understood by those skilled in the art that the dosage amount will vary with the severity of the condition, the age, size, the general condition of the patient, and like factors known in the medical art. In general, a suitable dose will be that amount of the compound which is the lowest dose effective to promote the quickest expulsion of ureteral stones or fragments without toxicity. However, a precise dosage may be determined by an attending physician within the scope of sound medical judgment.

EXAMPLES

The examples which follow illustrate exemplary embodiments of compositions and methods of the present invention.

Example 1

Representative Compositions

Representative compositions according to the present invention are shown below in Table 1.

TABLE 1

| Diazepam (%) | Methylcellulose | Hydroxyethylcellulose | Glycerin | PLO* |
|---|---|---|---|---|
| 1 | ✓ |  | ✓ |  |
| 1 | ✓ |  |  | ✓ |
| 1 |  | ✓ | ✓ |  |
| 1 |  | ✓ |  | ✓ |
| 2 | ✓ |  | ✓ |  |
| 2 | ✓ |  |  | ✓ |
| 2 |  | ✓ | ✓ |  |
| 2 |  | ✓ |  | ✓ |
| 3 | ✓ |  | ✓ |  |
| 3 | ✓ |  |  | ✓ |
| 3 |  | ✓ | ✓ |  |
| 3 |  | ✓ |  | ✓ |

*PLO is Pluronic lecithin organogel

As shown in Table 1, representative compositions according to the present invention may comprise diazepam typically ranging from about 1-3%, although in certain compositions less than 1% or more than 3% may be appropriate. Representative compositions also may contain methylcellulose or hydroxyethylcellulose in either glycerin or PLO or in some circumstances, combinations of any of the foregoing.

Such compositions can be delivered locally to the bladder or ureters to promote expulsion of ureteral calculi and fragments and to prevent re-formation of same.

Example 2

Effect of Diazepam Compositions on the Contractility of Human Isolated Ureter Human ureteral specimens (proximal end) were obtained from three female patients 50, 58 and 76 years old. These patients (negative for HIV 1-2, HTLV 1-2, hepatitis B-C and syphilis) had undergone nephrectomy because of renal pathologies in the Urology Departments of Rangueil Hospital (Toulouse, France). These tissues were donated following patient's written informed consent. Information on each patient's age, sex, body weight, height, anesthetics used during surgery, and nature of drugs administered in the 1-month period before hospitalization was obtained.

The specimens, which appeared macroscopically healthy, were placed in a cold storage solution (Custodiol®, OPI—France) immediately after surgery and transported to the laboratory facility in a box maintained at 4° C. Upon receipt, tissues were stored at 4° C. until the start of the experiment (maximum 24 hours after surgery).

Upon receipt, the test substance, diazepam, was inspected, logged in a cabinet and stored at room temperature. Each day of the experimentation, a stock solution of diazepam was prepared at a concentration of 0.1 M using DMSO as solvent. Diluted solutions containing the concentrations to be tested were prepared in distilled water.

Salts for preparing the were obtained from Prolabo-VWR international (94126 Fontenay-sous-bois, France). These salts were dissolved in distilled water. Dimethyl sulfoxide was purchased from Prolabo-VWR international (94126 Fontenay-sous-bois, France). Fresh solutions were prepared on each day of experimentation.

Tissues were immersed in 5 ml organ baths (EMKA Technologies, France). Contractile responses were measured using isometric tension transducers (it-1 EMKA Technologies, France) and recorded using a Chart version 4.2.3 software and a PowerLab 16s data acquisition system (ADInstruments Pty Ltd., Castle Hill, Australia), running on a PC computer. Electrical field stimulation (EFS) was performed through platinum electrodes connected to EMKA constant current, asynchronous stimulators (Model stm-b01, EMKA Technologies SA, Paris, France).

Specimens were cleared of adjacent tissues, cut into several rings (3-4 mm of diameter) and mounted, under 2 g initial tension, in 5 ml organ baths containing Krebs-Henseleit solution (composition in mM: NaCl 114, KCl 4.7, $CaCl_2$ 2.5, $MgSO_4$ 1.2, $KH_2PO_4$ 1.2, $NaHCO_3$ 25, glucose 11.7). The organ bath chambers were continuously aerated with 95% $O_2$ and 5% $CO_2$, the pH=7.4 and the temperature was maintained at 37±1° C. After 60 min of equilibration, smooth muscle rings were exposed to 80 mM KCl to measure their viability. Contractile responses were measured using isometric tension transducers and a computerized data acquisition system. EFS was performed through platinum electrodes connected to constant current, asynchronous stimulators.

Following 30 min of equilibration period, EFS was started. The EFS parameters were the following: constant current 300 mA, frequency 50 Hz, pulse width 2 ms, trains of 1 s every 30 s. After achieving a stable plateau of contraction, diazepam was tested in separate strips in cumulative concentrations in the range 0.1-30 µM. Time-matched control tissues were challenged with the corresponding volume of solvent (DMSO). At the end of the experiment, the maximal relaxant capacity of each tissue was checked by the addition of 10 µM forskolin, a potent activator of adenylate cyclase. In addition, some DMSO rings were challenged with tetrodotoxin to confirm that EFS-induced contractions were of myogenic, not neurogenic, origin.

Rings from one patient were used to calibrate the system. Rings from the other two patients were used to generate experimental data. All data were expressed as log of the molar concentration (log M). Results (see FIGS. 1 and 2) are expressed as mean±SEM of the residual contraction after each drug concentration (or solvent) on the basal level of contractions induced by EFS (determined 1 min before challenging organ baths with the test substance). Values were expressed as % inhibition EFS induced contraction. Statistical analysis of the results was performed by an unpaired t test.

Figure 2:
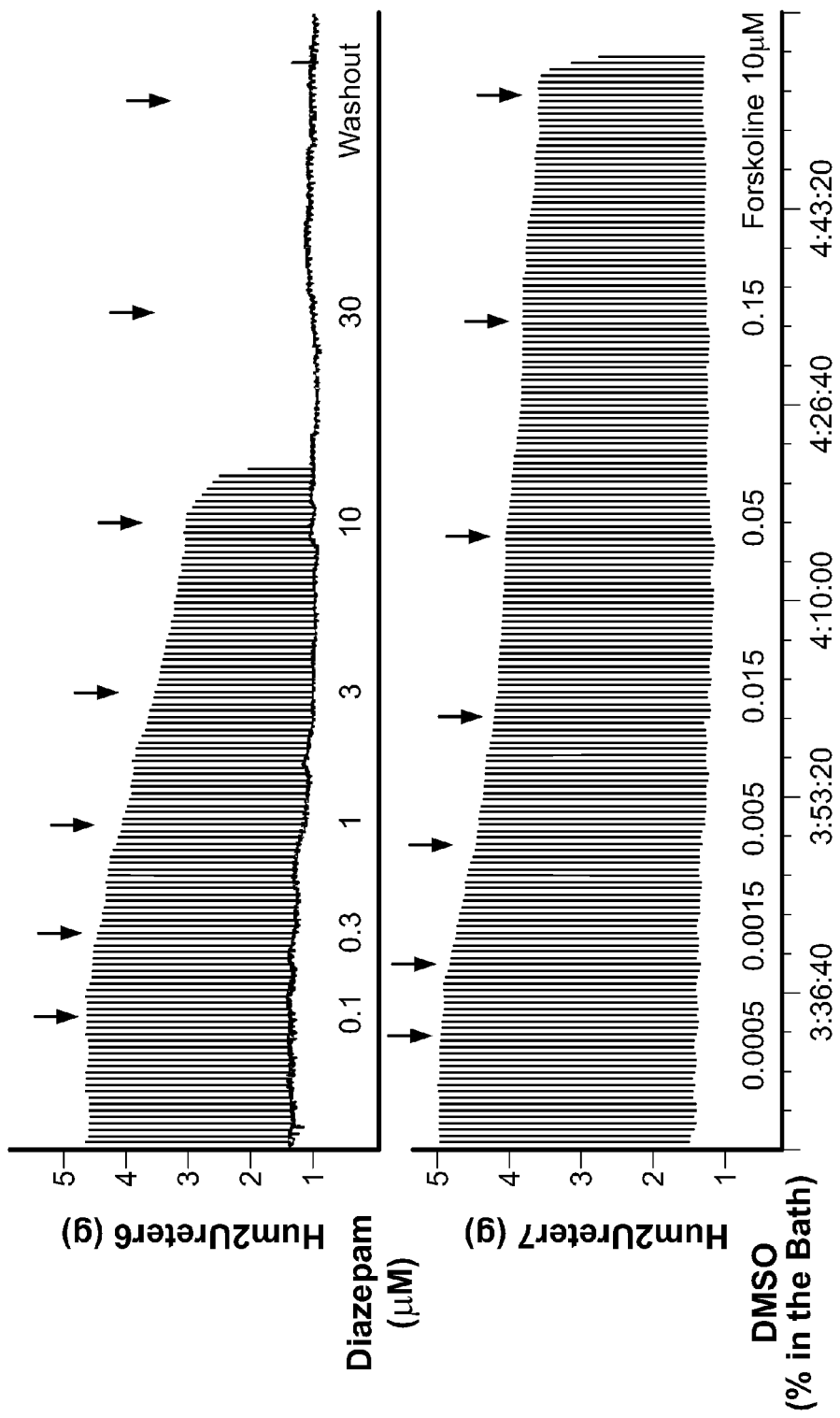
FIG. 2 shows EFS results of increasing concentrations of diazepam on isolated human ureter tissue.
Figure 3:
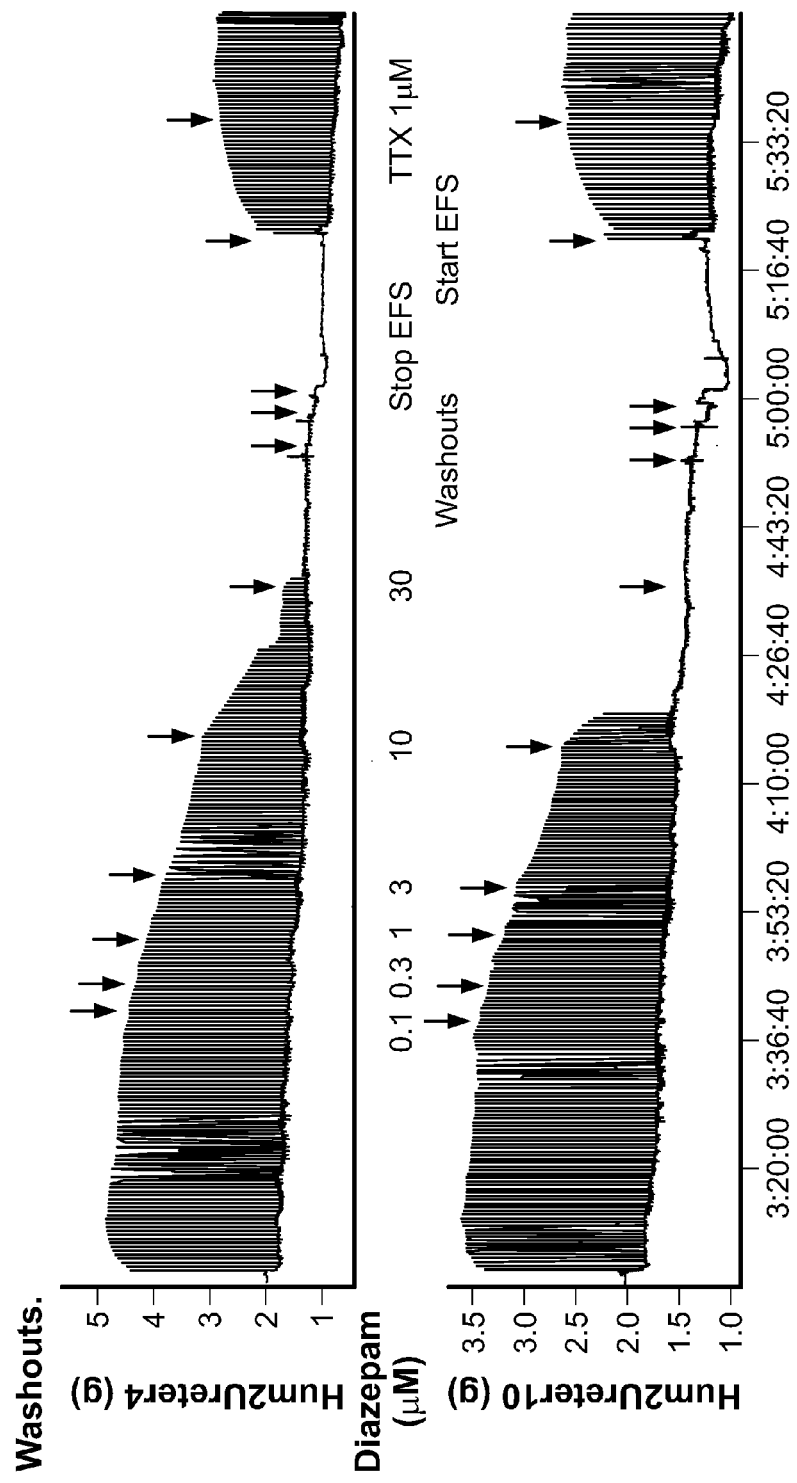
FIG. 3 shows the EFS results of increasing concentrations of diazepam on isolated human ureter tissue and the recovery of the EFS-induced contraction following diazepam-induced inhibition.

As shown in FIGS. 1 and 2, diazepam-containing preparations created a dramatic dose dependent inhibition of EFS-induced ureteral contractions. This was not observed with the solvent control. At the highest concentration tested (30 µM) diazepam abolished EFS-induced contractions. The maximal relaxant capacity of diazepam was significantly greater than control ($p<0.0001$). As shown in FIG. 3, following inhibition of EFS-induced contractions by diazepam, a rapid washout of tissue was sufficient to re-establish contractions.

These results demonstrate that local delivery of diazepam inhibits myogenic contraction induced by EFS on human ureteral smooth muscle. Importantly, the rapid recovery of EFS-induced contractions following diazepam washout shows that local delivery of diazepam is not harmful to ureteral tissue.

Example 3

Effect of Diazepam on the Ureteral Muscle of Rats and Humans

The study described in Example 3 assessed the relaxant effects of diazepam applied directly to ureteral muscle samples harvested from rats and humans.

Ureteral muscle rings obtained from women undergoing nephrectomy or ureteral muscle strips harvested from adult male Wistar rats (n=8 samples of each) were mounted in 5 mL organ baths containing Krebs-Henseleit solution. The organ baths were kept at 37±1° C. and continuously aerated with 95% O2-5% CO2. After 60 minutes of equilibration, smooth muscle samples were exposed to 80 or 30 mM KCl (human and rat, respectively) to assess their viability. After washout and 30 additional minutes of equilibration, electrical field stimulation (EFS) was started. After achieving a stable plateau of contraction, ureteral samples were exposed to diazepam in concentrations ranging from 0.1-30 µM. Time-matched controls were obtained exposing tissues to a solution of drug vehicle without diazepam (DMSO in distilled water). At the end of the experiment, the maximal relaxant capacities of each tissue were determined by exposure to 10 µM forskolin.

Diazepam inhibited EFS-induced contraction of human and rat ureters in a concentration-dependent manner. The concentration-response curves yielded pIC50 values of 5.35±0.07 and 5.95±0.16, respectively. The maximal relaxant effects (Emax) of diazepam were 98.4±0.2% and 67.4±5.0% of the basal response to EFS, respectively. Incubation of ureteral tissue in vehicle alone caused significantly less inhibition of EFS-induced contraction (Emax 31.4±1.7% for human and 16.2±4.4% for rat). In human ureter, following total inhibition of tissue contraction by diazepam, baseline EFS-induced contractility was restored after 3 washouts, suggesting that diazepam did not have sustained toxic effects on this tissue.

This Example shows that diazepam has direct, dose-related and reversible relaxant effects on ureteral smooth muscle from both humans and rats. Topically-applied diazepam may be used as a treatment for ureteral colic and as an expulsive agent to promote the passage of ureteral stones or of the stone fragments that persist, for example, following lithotripsy.

From the foregoing, it will be appreciated that, although specific embodiments of the present invention have been described herein for purposes of illustration, various modifications may be made without deviating from the spirit and scope of the invention. Accordingly, the present invention is not limited, except as by the appended claims.

The invention claimed is:

1. A method for treatment of kidney stones, ureteral stones and acute ureteral colic or renal colic in a mammal, said method comprising:
   administering into the bladder or ureter a locally effective amount of diazepam of said mammal for whom such treatment is needed or desirable.

2. The method of claim 1, wherein the mammal is a human.

3. The method of claim 1, wherein the effective amount of diazepam is administered by intraurethral injection or by instillation through a bladder catheter.

4. The method of claim 1, wherein the effective amount of diazepam promotes expulsion of ureteral stones.

5. The method of claim 1, wherein the effective amount of diazepam promotes expulsion of ureteral stone fragments.

6. The method of claim 1, wherein the effective amount of diazepam is less than 50 mg.

7. The method of claim 6, wherein the effective amount of diazepam comprises from about 1 mg to about 30 mg.

8. The method of claim 7, wherein the effective amount of diazepam comprises from about 5 mg to about 20 mg.

9. The method of claim 6, wherein the effective amount of diazepam comprises less than about 5 mg.

10. The method of claim 1, wherein following said administration combined plasma level of diazepam and desmethyldiazepam does not exceed about 100 ng/ml.

11. The method of claim 10 wherein following said administration the combined plasma level of diazepam and desmethyldiazepam does not exceed about 50 ng/ml.

12. The method of claim 11, wherein following said administration the combined plasma level of diazepam and desmethyldiazepam does not exceed about 25 ng/ml.

13. The method of claim 1, wherein the diazepam is administered as an adjuvant to extracorporeal shock wave lithotripsy (ESWL).

14. A pharmaceutical composition for the treatment of kidney stones, ureteral stones and colic associated therewith in a mammal comprising:
   diazepam and pharmaceutically acceptable excipients, wherein such dosage form is suitable for local administration into the bladder or ureter of said mammal in a locally effective amount to treat kidney stones, ureteral stones and colic associated therewith in said mammal.

15. The pharmaceutical composition of claim 14 in a form selected from the group consisting of suppositories, ointments, solutions, gels, sprays, creams, suspensions, liquids, powders and pastes and any combination thereof.

16. The pharmaceutical composition of claim 15 in the form of a gel.

17. The pharmaceutical composition of claim 16, wherein the gel is a matrix-based gel.

* * * * *